United States Patent [19]

Obrero et al.

[11] Patent Number: 4,771,571

[45] Date of Patent: Sep. 20, 1988

[54] METHOD FOR TREATING PINEAPPLE TO PREVENT PINEAPPLE FRUIT DISEASES

[75] Inventors: Faustino P. Obrero; Wilfred Schnitzler, both of Manila, Philippines

[73] Assignee: Nabisco Brands, Inc., Parsippany, N.J.

[21] Appl. No.: 948,322

[22] Filed: Dec. 31, 1986

[51] Int. Cl.$^4$ ............................................. A01N 5/00
[52] U.S. Cl. ................................... 47/58; 47/DIG. 11
[58] Field of Search ........................... 47/58, DIG. 11

[56] References Cited

U.S. PATENT DOCUMENTS

| | | |
|---|---|---|
| 1,529,461 | 3/1925 | Brogden et al. |
| 1,903,283 | 4/1933 | Brogden et al. |
| 2,332,151 | 10/1943 | Kalmer |
| 2,427,857 | 9/1947 | Hamill |
| 2,503,663 | 4/1950 | Gericke |
| 2,849,320 | 8/1958 | Weinmann |
| 3,037,867 | 10/1962 | Daudin ................................. 99/168 |
| 3,556,814 | 1/1971 | Whitman |
| 3,847,641 | 11/1974 | Cushman et al. ............. 47/DIG. 11 |
| 4,006,259 | 2/1977 | Kalmar |
| 4,434,185 | 2/1984 | Nelson .............................. 426/308 |
| 4,681,617 | 7/1987 | Ghyczy et al. ................ 47/DIG. 11 |

FOREIGN PATENT DOCUMENTS

| | | | |
|---|---|---|---|
| 19393 | 8/1965 | Japan | 47/DIG. 11 |
| 134403 | 8/1982 | Japan | 47/DIG. 11 |
| 1121265 | 4/1982 | Canada | 47/DIG. 11 |

OTHER PUBLICATIONS

Kader et al., Hort. Science 14(3): 471, Abstract (1979).
S. K. Wolfe, Food Technology, 34(3): 55–58 (1980).
N. Sommer, Plant Disease, 66(5) 357–364 (1982).
M. A. El-Goorani, Hort. Review 3:412–461 (1981).
Le Grice et al., Phytophylactical, 63–64 (1970).

Primary Examiner—Robert E. Bagwill
Attorney, Agent, or Firm—Richard Kornutik

[57] ABSTRACT

Ripening pineapple fruit in the field is treated with effective amounts of an aqueous solution of a nonionic surfactant to inhibit infection of the pineapple fruit by disease-causing microorganisms. Microbial spoilage is reduced, and thus the quality of pineapple fruit for the fresh market is improved. Additionally, disease blemishes in pineapple fruits for canning are reduced, resulting in increased pineapple solids recovery.

8 Claims, No Drawings

METHOD FOR TREATING PINEAPPLE TO PREVENT PINEAPPLE FRUIT DISEASES

This invention pertains to a method for treating ripening pineapple fruit in the field to inhibit infection by disease-causing microrganisms.

BACKGROUND OF THE INVENTION

Ripening pineapple fruit is susceptible to infection by a variety of disease-causing microorganisms. Such diseases tend to develop and damage the fruit during fruit maturation starting from 20 days before the fruits are harvested until they reach the consumer as fresh fruit or are processed in the cannery as canned pineapple. Thus, the internal quality of fresh fruit is reduced and fruit solid recovery in the cannery may be significantly decreased due to attack by such microorganisms as Acetomonas sp., and *Erwinia herbicola,* which are believed to cause pineapple pink disease. Other deteriorating pineapple diseases resulting from microbial action include marbling, which is believed to be caused by species of Acetobacter. and fruitlet-core rot (black spot), which is is believed to be caused by a complex of microorganisms such as Penicillium sp., and Fusarium sp., bacteria, and yeasts.

It is known in the art that the deterioration of fruit by microbial action, e.g. fungus or bacterial growth, can be inhibited by subjecting the fruit after harvesting to an atmosphere having a low oxygen and high carbon dioxide content. See, A. A. Kader, M. A. El-Govrani, and N. F. Sommer, *Effect of CO+ Elevated $CO_2$ and/or Reduced $O_2$ Levels on Postharvest Behavior and Quality of Peaches,* Vol. 14(3) Hort Science (1979), p. 471.

Accordingly, efforts have been made to create a micro-environment which is unfavorable for the growth of fruit microorganisms, for example, by applying a coating of wax to the surface of the harvested fruit. However, the use of wax is often objectionable from a consumer standpoint, because the color, texture, or flavor of the fruit is often undesirably effected by the wax coating. Additionally, it is difficult to apply such wax coatings evenly over the surface of the fruit without using so much wax that the normal "breathing" of the fruit is interfered with to an undesirable extent.

SUMMARY AND OBJECTS OF THE INVENTION

Accordingly, it is an object of the present invention to provide a method for treating pineapple fruit which is effective for inhibiting the growth of pineapple disease-causing microorganisms.

A further object of the invention is to provide a method for controlling microbial spoilage of pineapple fruit by coating the ripening fruit in the field with aqueous solutions of certain non-phytotoxic and nonionic surfactants, in the absence of added wax.

These objects and other subsidiary objects which will be apparent to those skilled in the art are achieved by the practice of the present invention.

The present invention provides a method for treating pineapple plants to control pineapple fruit diseases caused by microbial action, which comprises the step of treating the ripening fruit in the field prior to harvesting with effective amounts of an aqueous solution of a non-ionic, non-phytotoxic surfactant, to inhibit infection of the fruit by pineapple fruit disease-causing microorganisms, wherein the surfactant is selected from the group consisting of ethoxylated natural fats and oils, ethoxylated alkylphenols, ethoxylated glycerol esters of fatty acids, polyoxyethylene fatty acid esters, and mixtures thereof. Microbial spoilage of the fruit is arrested, thus improving the internal quality of pineapple fruit intended for sale in the fresh fruit market. Additionally, disease blemishes in the fruit are reduced, so that increased fruit solid recovery in the cannery is made possible.

DETAILED DESCRIPTION OF THE INVENTION

While the invention is susceptible to various modifications and alternative forms, there will be described herein the preferred embodiments.

The present invention provides a method for inhibiting the infection of ripening pineapple fruit by rot and disease causing microorganisms. Accomplishment of this desirable goal is achieved by coating the surface of the pineapple fruit in the field with effective amounts of an aqueous solution of certain surfactants.

As understood by those skilled in the art, the term "surfactant" is used to describe a variety of amphipathic molecules composed of separated groups having opposing solubilizing tendencies. For example, a surfactant may contain an oil-soluble hydrocarbon chain separated by a suitable degree from a water-soluble ionic group. C. Arno and J. Lynn, Jr., *Surfactants and Detersive System,* vol. 22 *Encyclopedia of Chemical Technology* 3rd ed. (Kirk-Othmer 1983), pp. 332–336.

Surfactants are generally classified according to the charge of the larger group in the molecule. In anionic surfactants, this moeity carries a negative charge, while in cationic surfactants the charge is positive. Nonionic surfactants carry no charge, and the solubilizing contribution is usually supplied by a chain of ethylene oxide groups. In amphoteric surfactants, on the other hand, solubilization is provided by the presence of both positively and negatively charged groups.

Although there are a wide variety of surfactants, tests have indicated that only certain ones of these, or mixtures thereof, are suitable for use in the present invention. The surfactants, which are non-phytotoxic in the usual concentrations in which they are applied, are preferably nonionic surfactants selected from the group consisting of ethoxylated glycerol esters of fatty acids, polyoxyethylene fatty acid esters, ethoxylated natural fats and oils, ethoxylated alkylphenols, and mixtures thereof.

While not wishing to be limited to a particular theory or mode of action, it is believed that the surfactant when applied provides a seal over substantially all of the fruit's surface, thereby creating an internal fruit micro-environment of low oxygen and high carbon dioxide content which is unfavorable for the growth and reproduction of pineapple disease microorganisms and the development of fruit-disease symptoms. It is believed that the applied surfactant also causes the natural waxes present on the surface of the fruit to become evenly distributed over the fruit surface. Thus, the sealing effects provided by the natural waxes present on the fruit surface are enhanced.

Additionally, it has been found that the seal on the surface of the fruit formed by the surfactant coating also prevents the escape of fruit esters from the ripening fruit. Consequently, the freshness of the fruit is maintained from the time the fruit is harvested until it reaches the consumer.

The following two surfactant have been found particularly effective at inhibiting infection of pineapple fruit by disease-causing microorganisms:

1. TANDEM ® 552, a blend of mono and diglycerides, and polyoxyethylene sorbitan monostearates, which is commercially available from Kraft Inc., U.S. and which is presently patented as a liquid dough strengthener and crumb softener for yeast-raised baked goods (U.S. Pat. No. 3,785,993); and
2. AGRISOL SP 100 TM, an emulsifier blend of monoglyceride and polyoxyethylene fatty acid esters which is commercially available from KAO Corporation, Japan.

Other surfactants, such as LUTENSOL A-8 TM (an ethoxylation product of fatty alcohols based on coconut oil, which is commercially available from BASF, AG, West Germany); TRITON X-45 TM (an octyl phenoxy polyethoxy ethanol commercially available from Rohm & Haas, U.S.); and LOVING KL TM (a food detergent containing sucrose mono and dioleates, potassium pyrophosphate and phosphoric acid, which is commercially available from KAO Corporation, Japan); as well as several vegetable and mineral oils, were found to be useful but less effective in controlling microbial spoilage than the preferred surfactants listed above.

For the prevention of pineapple fruit diseases according to the invention, an aqueous solution having a surfactant concentration of about 5% by weight is preferably utilized. The solution is applied to the ripening fruit in the field, prior to harvesting, by such methods as spraying with knapsack or boom sprayers, or pouring, so as to ensure coating of substantially all of the fruit's surface. Although the amount of surfactant required per ton of fruit will vary depending on the size of the fruit, etc., the aqueous solution is preferably applied at a rate of about 400 gallons per acre. Additionally, the surfactant-containing solution is preferably applied about twenty days before the pineapple fruit is harvested.

The invention does not alter the conventional techniques employed in the harvesting, storage, shipment, and marketing of pineapple fruit treated according to the invention. Thus, the temperature and humidity conditions normally used for preserving the freshness of the harvested fruit are suitable for use in connection with the invention.

By treating fruit with an aqueous, surfactant-containing solution in accordance with the invention, deterioration of the pineapple fruit by disease-causing microorganisms is arrested, and the internal quality of fresh pineapple fruits is improved and the marketable life of the subsequently harvested fruit is extended. Also, disease blemishes in pineapple fruits for the cannery is reduced, thus increasing recovery of pineapple fruit solids. Additionally, the escape of fruit essences from the ripening fruit is inhibited.

What is claimed is:

1. A method for controlling pineapple fruit diseases caused by microbial action, which comprises the step of treating the ripening pineapple fruit in the field with effective amounts of "a wax-free" aqueous solution of a non-phytotoxic, non-ionic surfactant to inhibit infection of the fruit by pineapple fruit disease-causing microorganisms, wherein the surfactant is selected from the group consisting of glycerol esters, polyoxyethylene fatty acid esters of fatty acids, and ethoxylated natural fats and oils, ethoxylated alkylphenols, and mixtures thereof.

2. The method according to claim 1, wherein the aqueous solution is applied by spraying.

3. The method according to claim 1, wherein the aqueous solution is applied about twenty days before the pineapple fruit is harvested.

4. The method according to claim 1, wherein the aqueous solution is about 5% surfactant by weight.

5. The method according to claim 4, wherein the aqueous solution is applied at a rate of about 400 gallons per acre.

6. The method according to claim 1, wherein the pineapple fruit disease is selected from the group consisting of fruitlet-core rot, marbling, and pink disease.

7. The method according to claim 1, wherein the amount of aqueous solution applied is also effective to inhibit escape of the pineapple esters present in the ripening fruit and increase recovery of pineapple fruit solids for canning.

8. The method according to claim 1, wherein the surfactant is selected from the group consisting of TANDEM ® 552, AGRISOL SP 100 TM, and mixtures thereof.

* * * * *